United States Patent
Mandel

(10) Patent No.: US 7,981,078 B2
(45) Date of Patent: Jul. 19, 2011

(54) INFLATION/DEFLATION SYSTEM FOR A CATHETER

(75) Inventor: Moshe Mandel, Doar Afek (IL)

(73) Assignee: Mego Afek AC Ltd., Doar Afek (IL)

( * ) Notice: Subject to any disclaimer, the term of this patent is extended or adjusted under 35 U.S.C. 154(b) by 0 days.

(21) Appl. No.: 12/073,496

(22) Filed: Mar. 6, 2008

(65) Prior Publication Data

US 2009/0018499 A1 Jan. 15, 2009

Related U.S. Application Data

(60) Provisional application No. 60/929,667, filed on Jul. 9, 2007.

(51) Int. Cl.
*A61M 29/00* (2006.01)

(52) U.S. Cl. ........... 604/100.03; 604/100.01; 604/96.01; 604/121

(58) Field of Classification Search ............ 604/26, 604/247–249, 97.01–98.02, 99.01–100.01, 604/100.03, 920; 251/319, 324, 330, 325, 251/339, 318
See application file for complete search history.

(56) References Cited

U.S. PATENT DOCUMENTS

| | | | |
|---|---|---|---|
| 5,273,537 A | 12/1993 | Haskvitz et al. | |
| 5,284,480 A | 2/1994 | Porter et al. | |
| 5,342,298 A * | 8/1994 | Michaels et al. | 604/65 |
| 5,599,301 A | 2/1997 | Jacobs et al. | |
| 5,755,686 A * | 5/1998 | O'Neill et al. | 604/508 |
| 5,891,089 A | 4/1999 | Katz et al. | |
| 6,299,592 B1 * | 10/2001 | Zander | 604/26 |
| 6,918,893 B2 * | 7/2005 | Houde et al. | 604/248 |
| 7,497,843 B1 * | 3/2009 | Castillo et al. | 604/152 |
| 2007/0197963 A1 * | 8/2007 | Griffiths et al. | 604/97.01 |

FOREIGN PATENT DOCUMENTS

| | | |
|---|---|---|
| DE | 19909654 A1 | 7/2000 |
| EP | 0213765 A2 | 3/1987 |
| EP | 0275638 A2 | 7/1988 |
| EP | 0576380 A1 | 12/1993 |

(Continued)

*Primary Examiner* — Nicholas D Lucchesi
*Assistant Examiner* — Leah Stohr
(74) *Attorney, Agent, or Firm* — The Nath Law Group; Susanne M. Hopkins; Jiaxiao Zhang

(57) ABSTRACT

According to the present invention there is provided an inflation/deflation system for a dilatation balloon comprising a receptacle, a pressure member, a sensing system and a data processing and display unit. The receptacle is adapted to contain an inflation fluid to be introduced into the balloon during its inflation. The receptacle also has an inlet/outlet port adapted for connection to the dilatation balloon; The pressure member is adapted to be axially displaced within the receptacle to cause the fluid to exit the receptacle via the outlet port. The sensing system comprises a first sensor and a second sensor. The first sensor is associated with the pressure member to sense its axial displacement. The second sensor is associated with the interior of the receptacle to sense in a non-contact manner the pressure P of the inflation fluid within the receptacle, and to provide a corresponding data signal. The data processing and display unit is adapted to process the signal and display at least a scheme of pressure P within the receptacle vs. the volume V of the inflation fluid exiting the receptacle through the inlet/outlet port. The volume is calculated by the axial displacement of the pressure member. The scheme reflects the corresponding P-V conditions within the balloon when the system is in use.

30 Claims, 6 Drawing Sheets

FOREIGN PATENT DOCUMENTS

| | | |
|---|---|---|
| EP | 1199083 A1 | 4/2002 |
| WO | WO98/57694 A1 | 12/1998 |
| WO | WO00/44431 A1 | 8/2000 |
| WO | WO02/064195 A2 | 8/2002 |
| WO | WO2007/002154 A2 | 1/2007 |
| WO | WO2007/076463 A2 | 7/2007 |
| WO | WO2008/042347 A2 | 4/2008 |

* cited by examiner

US 7,981,078 B2

INFLATION/DEFLATION SYSTEM FOR A CATHETER

This application claims the benefit of prior U.S. provisional patent application No. 60/929,667 filed Jul. 9, 2007, the contents of which are hereby incorporated by reference in their entirety

FIELD OF THE INVENTION

This invention relates to angioplasty systems, in particular to catheter balloon inflation/deflation systems controlled to perform a balloon inflation/deflation process according to predetermined parameters.

BACKGROUND OF THE INVENTION

Dilatation balloons and systems for their dilatation are known in the art in the field of angioplasty, where the balloons are usually used to dilate a blood vessel by inserting the balloon into the blood vessel and inflating it by introducing inflation liquid into the balloon. Such systems and processes are also commonly referred to respectively as catheter balloon and catheterization.

In the course of a catheterization process, a variety of malfunctions may take place including rupture of the balloon, leakage in the balloon and even a rupture of the blood vessel into which the balloon is inserted. In such cases, the inflation fluid may pour into the blood vessel or into the body. For this reason, it is usually desirable to keep the inflation liquid sterilized.

U.S. Pat. No. 5,273,537 discloses an inflation apparatus which is economically returnable to a sterile state after use, and which provides easy, accurate control over pressure within the dilatation balloon.

The inflation apparatus for inflating a dilatation balloon includes a frame having a first receiver supporting the barrel of a syringe. An operator has a second receiver supporting the plunger of the syringe. The syringe includes a fluid port for connecting the syringe chamber to the lumen of the catheter. A motor is supported by the frame and operatively connected to the operator to move the piston to change fluid pressure within said syringe chamber. A release device permits quick release of the pressure in the balloon catheter without the use of the motor. A pressure sensor is mounted to the frame to measure the pressure in the chamber through a diaphragm on the syringe. The pressure sensor operates a microprocessor-controlled display, which provides display of inflation and duration information and calculates other information. A circuit selectively operates the motor. An inflation control connected to the circuit permits operation of the motor at selected rates of inflation/deflation or to selected specific inflation pressures.

In most catheterization processes it is beneficial to use inflation cycles in order to gradually dilate the blood vessel. It is also preferable to maintain a steady inflation/deflation rate for the same reason. For this purpose, a number of motorized catheter systems have been suggested. In some of the latter systems, feedback data regarding pressure and time at which the inflation fluid is introduced into the balloon is also provided using sensors.

For example, in U.S. Pat. No. 5,599,301 a motor controller for providing a constant rate of pressure change during inflation and deflation of an expandable member of a catheter for use in a body lumen by an automated inflation system is disclosed. The system conforms the rate of change of pressure to a set point value by means of a feedback loop controller, and makes possible consistent inflations and deflations using an automated system regardless of variations in catheter volume and compliance characteristics. Safety features such as maximum pressure and balloon rupture alarms are also disclosed.

Various improvements of sensing systems for catheter inflation systems have been suggested, for example in U.S. Pat. No. 5,891,089 disclosing a fluid pressure sensing and activating control system for coronary angioplasty, including a fluid pressure sensor and transducer connected to feed signals via an A/D converter to a processor and control unit, a pulse width generator receiving signals from the processor for activating a balloon inflator, and a fluid conduit connector attached to the output of the inflator and to the input of the fluid pressure sensor and transducer, and having a further output port connectable to an inflatable balloon. A method for dilating a section of an elastic conduit by means of an inflatable balloon inserted therein is also disclosed.

SUMMARY OF THE INVENTION

According to one aspect of the present invention there is provided an inflation/deflation system for a dilatation balloon, said system comprising
 a receptacle adapted to contain an inflation fluid to be introduced into said balloon during its inflation, said receptacle having an inlet/outlet port adapted for connection to said dilatation balloon;
 a pressure member adapted to be axially displaced within said receptacle to cause said fluid to exit the receptacle via said outlet port;
 a sensing system comprising a first sensor associated with said pressure member to sense its axial displacement, and a second sensor associated with the interior of said receptacle to sense in a non-contact manner the pressure P of the inflation fluid within said receptacle, and to provide a corresponding data signal; and
 a data processing and display unit adapted to process said signal and display at least a scheme of pressure P within said receptacle vs. the volume V of the inflation fluid exiting said receptacle through said inlet/outlet port, calculated by said axial displacement, said scheme reflecting the corresponding P-V conditions within the balloon when the system is in use.

In particular, the first sensor of the sensing system which is associated with the pressure member and adapted to measure its axial displacement, provides data allowing calculation of the volume V of fluid exiting the receptacle and consequently introduced into the balloon. For example, the amount of axial displacement L and cross section area C of the receptacle may be used in calculating the volume, i.e. V=L*C. The second sensor of the sensing system may be attached to the receptacle and adapted to measure the pressure of the fluid therein in a non-contact manner.

For example, the receptacle may have a pressure sensitive surface, e.g. a resilient end wall, and the second sensor may be in the form of a load cell attached to this wall to sense the load exerted on the resilient wall by the fluid within the receptacle via the deformation of the resilient wall. The load measurement may then be used in calculating the pressure within the receptacle. The sensing system may further comprise an additional sensor, also in the form of a load cell, adapted to measure the load on the pressure member. The additional sensor may be used for tuning of the pressure measurement by the sensing system by comparing its measurement and the measurement of said second sensor.

Since the axial movement mechanism is attached to the pressure member on one hand and to the sensor on the other, real-time data regarding the time of inflation and volume of the inflation fluid introduced into the balloon may be derived.

Real-time data as described above may provide important information to the operator of the inflation/deflation system. In particular, the P-V display may indicate breakage of plaque along the blood vessel being dilated, possible rupture of the dilatation balloon, a minor puncture therein, or leakage in any other part of the system. Thus, for example, when a P-V drops, this might indicate a hole in the dilatation balloon.

It should be noted that in a manual inflation/deflation system without a P-V display, in the case of a minor puncture in the dilatation balloon, and operator would notice either that the pressure ceases to increase or increases at a slower rate, and will consequently simply apply more pressure to the pressure member when, in reality, the inflation fluid is simply leaking out of the balloon into the blood vessel.

Another example in which the P-V scheme may provide information as to the catheter process is the case when breakage of plaque occurs along the blood vessel. The plaque is essentially a layer accumulating on the inside wall of a blood vessel. In the course of a dilatation process, this layer may break. This effect causes the blood vessel to become very sensitive and less resistant to pressure due to the plaque layer being broken and having sharp edges pressing against the wall of the blood vessel.

In the process of dilatation of the balloon and breakage of plaque as described above, the P-V curve may demonstrate a slight temporary slope drop and subsequent rise thereafter. This may alert the operator of the process to take heed and, for example, slow down the dilatation process in order to reduce damage the now sensitive inner wall of the blood vessel.

The system may further comprise a control unit associated on one hand with the data processing and display unit and adapted to receive processed data therefrom, and on the other hand with the motor in order to control it. Thus, a pre-programmed operation of the inflation/deflation system according to a desired P-T curve may be established. For example, the system may be programmed to reach a predetermined pressure within a predetermined amount of time. Furthermore, the inflation/deflation system may be adapted to work in predetermined cycles according to preset time and pressure parameters.

A major advantage of the system to perform the above described operations is that it may allow a technician, i.e. a person not skilled in the medical arts, to prepare the system for a doctor or a member of a medical staff, including its tuning, wherein said doctor or staff member may only be required to select the proper balloon and perform the insertion of the dilatation balloon and inflation thereof.

The system may comprise a base, which may be a multi-use part, and a disposable part, said base containing an actuation section comprising an actuator for moving said pressure member, said actuation section being disposed within a housing. Said base further comprises at least said sensing system, and said disposable part comprises the receptacle and the pressure member.

The base of said inflation/deflation system may further comprise a motor associated with said actuator and disposed within said housing. The motor may also be adapted to be connected to the first sensor of said sensing system in order to indirectly provide data about axial displacement of the pressure member, and subsequently allowing calculation of volume of inflation fluid discharged during the dilatation process.

Optionally, base may be made of at least a first and a second, such that when said disposable part is attached to said base, the receptacle thereof is attached to the first part and the pressure member is attached to the second part.

The base may further comprise a quick release mechanism allowing the manual separation of the pressure member from the receptacle without the use of a motor, in order to reduce the balloon pressure. The quick release mechanism may be in the form of a handle attached to said disposable part and adapted to manually pull back the pressure member, for example, by separating said first part of the base attached to the receptacle from said second part of the base attached to the pressure member.

It should be noted that the motors and sensors of the system are all part of the base whereby no contact between the inflation fluid and the base of the system is provided, thus eliminating the need to sterilize the base after each use of the system.

The receptacle may be in the form of a syringe barrel and said pressure member may be in the form of a syringe piston positioned therein, the barrel being adapted to receive an inflation fluid directly through said outlet port and contain said inflation fluid therein.

The disposable part may further comprise a disposable four-way valve, comprising main channel having at least a first, a second and a third port, a switch shaft adapted to axially displace therein to alternately open/close said ports. Said storage chamber may be fluid communication with said channel through one of said ports. The storage chamber may be adapted for removal of air from the inflation liquid, and may be in fluid communication with barrel of the receptacle via said channel. Said storage chamber may further comprise at least one additional port adapted to allow discharge of air from the inflation fluid to the outside environment. According to a specific design variation, the valve may be integrally formed with the receptacle to form said disposable part.

Thus, the four way valve may be adapted to allow at least four positions as follows:
a) 'inflation/withdrawal'—fluid communication is provided between the receptacle and the inlet/outlet port, while fluid communication with the storage chamber is blocked, allowing to withdraw inflation fluid from an outside source or administering it into the balloon;
b) 'air removal'—fluid communication is provided between the receptacle and the storage chamber, while fluid communication with the inlet/outlet port is blocked, allowing removal of air from the inflation fluid through the storage chamber;
c) 'tuning'—fluid communication is blocked both between the receptacle and inlet/outlet port and between the receptacle and storage chamber, allowing tuning of the load cells; and
d) 'discharge'—fluid communication is provided between the inlet/outlet port and receptacle to the outside environment through said channel, allowing removal of inflation fluid from the system during an emergency;

The switch-shaft may be adapted to be displaced within the channel, for example by a driving member such as a motor, which may be disposed in the housing of the actuation section of the base, allowing the valve to assume its various positions.

It should also be noted that the disposable part may be in the form of a 'ready to use' kit wherein the receptacle already contains the inflation fluid. In this case, no preparation is necessary other than connecting the disposable part to the base part, and performing tuning.

According to another aspect of the present invention there is provided a disposable kit for use with a base of an inflation/deflation system adapted for inflation of a dilatation balloon, and comprising:

a receptacle adapted to contain an inflation fluid to be introduced into said balloon during its inflation, said receptacle having an inlet/outlet port adapted for connection to said dilatation balloon;

a pressure member adapted to be axially displaced within said receptacle to cause said fluid to exit the receptacle via said outlet port; and the base of said system comprising:

a sensing system comprising a first sensor associated with said pressure member to sense its axial displacement, and a second sensor associated with the interior of said receptacle to sense in a non-contact manner the pressure P of the inflation fluid within said receptacle, and to provide a corresponding data signal; and a data processing and display unit adapted to process said signal and display at least a scheme of pressure P within said receptacle vs. the volume V of the inflation fluid exiting said receptacle through said inlet/outlet port, calculated by said axial displacement, said scheme reflecting the corresponding P-V conditions within the balloon when the system is in use.

According to a further aspect of the present invention there is provided a multi-use base for use in an inflation/deflation system for inflation of a dilatation balloon, with a disposable part comprising:

a receptacle adapted to contain an inflation fluid to be introduced into said balloon during its inflation, said receptacle having an inlet/outlet port adapted for connection to said dilatation balloon;

a pressure member adapted to be axially displaced within said receptacle to cause said fluid to exit the receptacle via said outlet port; and said multi-use part comprising:

a sensing system comprising a first sensor associated with said pressure member to sense its axial displacement, and a second sensor associated with the interior of said receptacle to sense in a non-contact manner the pressure P of the inflation fluid within said receptacle, and to provide a corresponding data signal; and a data processing and display unit adapted to process said signal and display at least a scheme of pressure P within said receptacle vs. the volume V of the inflation fluid exiting said receptacle through said inlet/outlet port, calculated by said axial displacement, said scheme reflecting the corresponding P-V conditions within the balloon when the system is in use.

According to still another aspect of the present invention there is provided a liquid distribution valve comprising a cylindrical body having a first end and a second end, at least two outlets disposed along said body, and a switch shaft adapted to be displaced within said body so as to alternately provide/shut off fluid communication between said at least two outlets, said valve further comprising a sealing element associated with said switch-shaft and adapted to prevent leakage of said liquid from said first end, and wherein said sealing element is adapted to be partially removed from said cylindrical body so as to allow fluid communication between said first end at least one of said two outlets.

BRIEF DESCRIPTION OF THE DRAWINGS

In order to understand the invention and to see how it may be carried out in practice, embodiments will now be described, by way of non-limiting examples only, with reference to the accompanying drawings, in which.

DETAILED DESCRIPTION OF EMBODIMENTS

Figure 1:
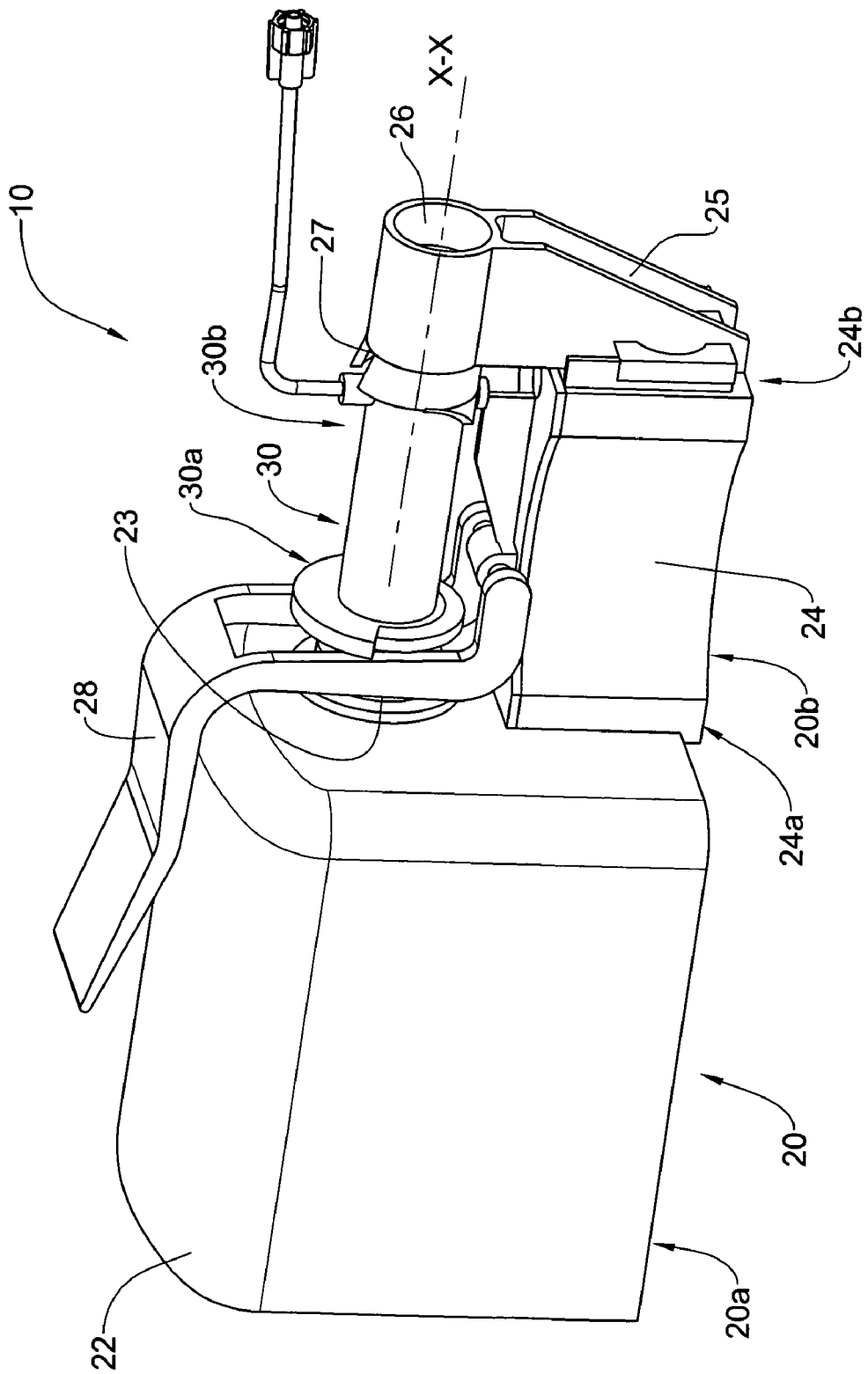
FIG. 1 is a schematic view of an inflation/deflation system according to one example of the present invention, having a multi-use part and a disposable part.

FIG. 1 shows an inflation/deflation system generally designated 10 comprising a base 20 including an actuation section 20a and a support section 20b, and a disposable part 30 detachably mounted on the base along their common central axis X. The disposable part 30 has a proximal end 30a detachably supported by the actuation section 20a, a distal end 30b detachably supported by the support section 20b, and a port 49 formed therein adjacent to the distal end 30b adapted for mounting thereon an inlet/outlet tube 60 as shown, for introducing inflation fluid into the disposable part and discharging the inflation fluid therefrom into a dilatation balloon (not shown).

Figure 2A:
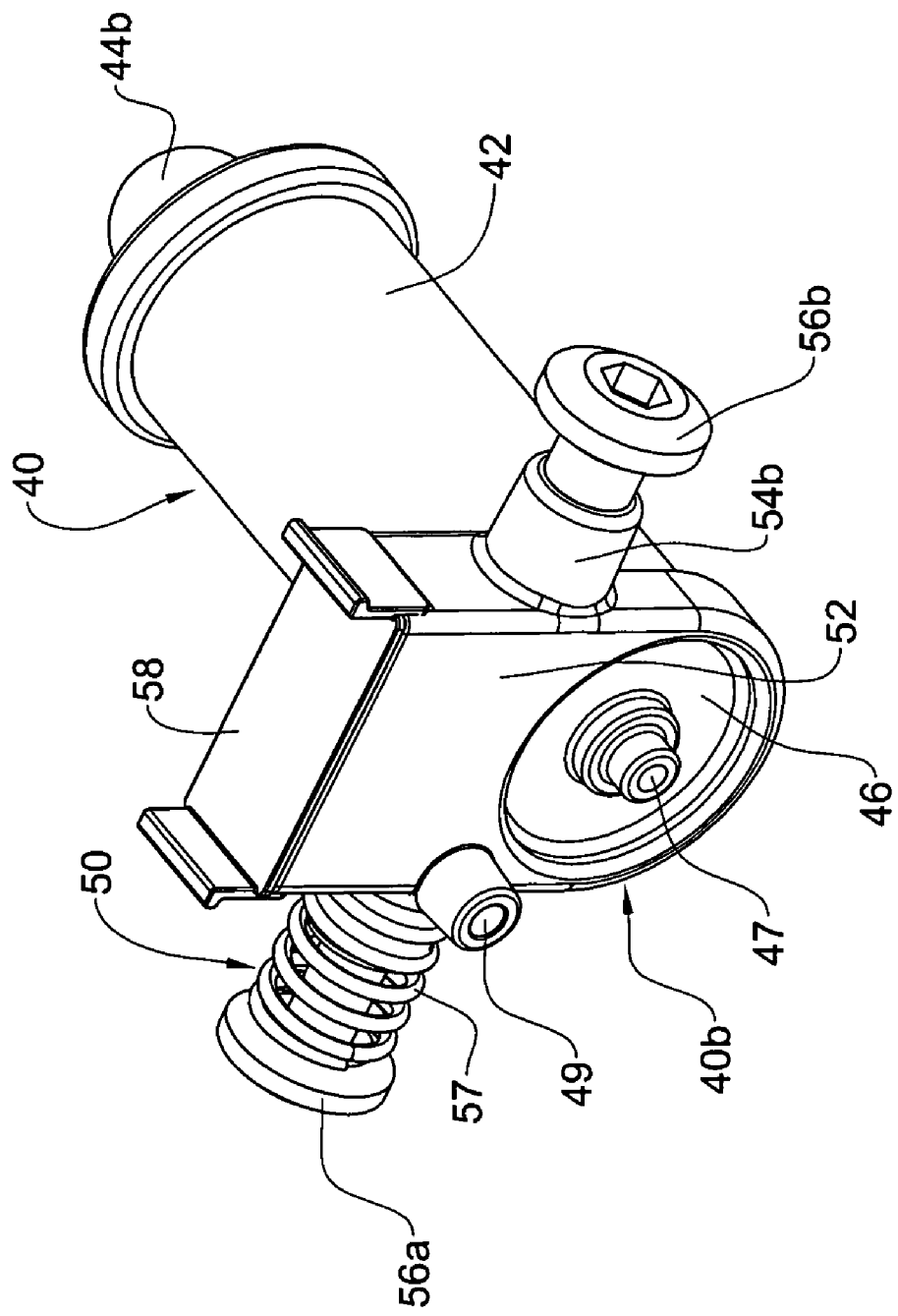
FIG. 2A is a schematic isometric view of the disposable part of the inflation/deflation system shown in FIG. 1 with an integrated valve assembly.
Figure 2B:
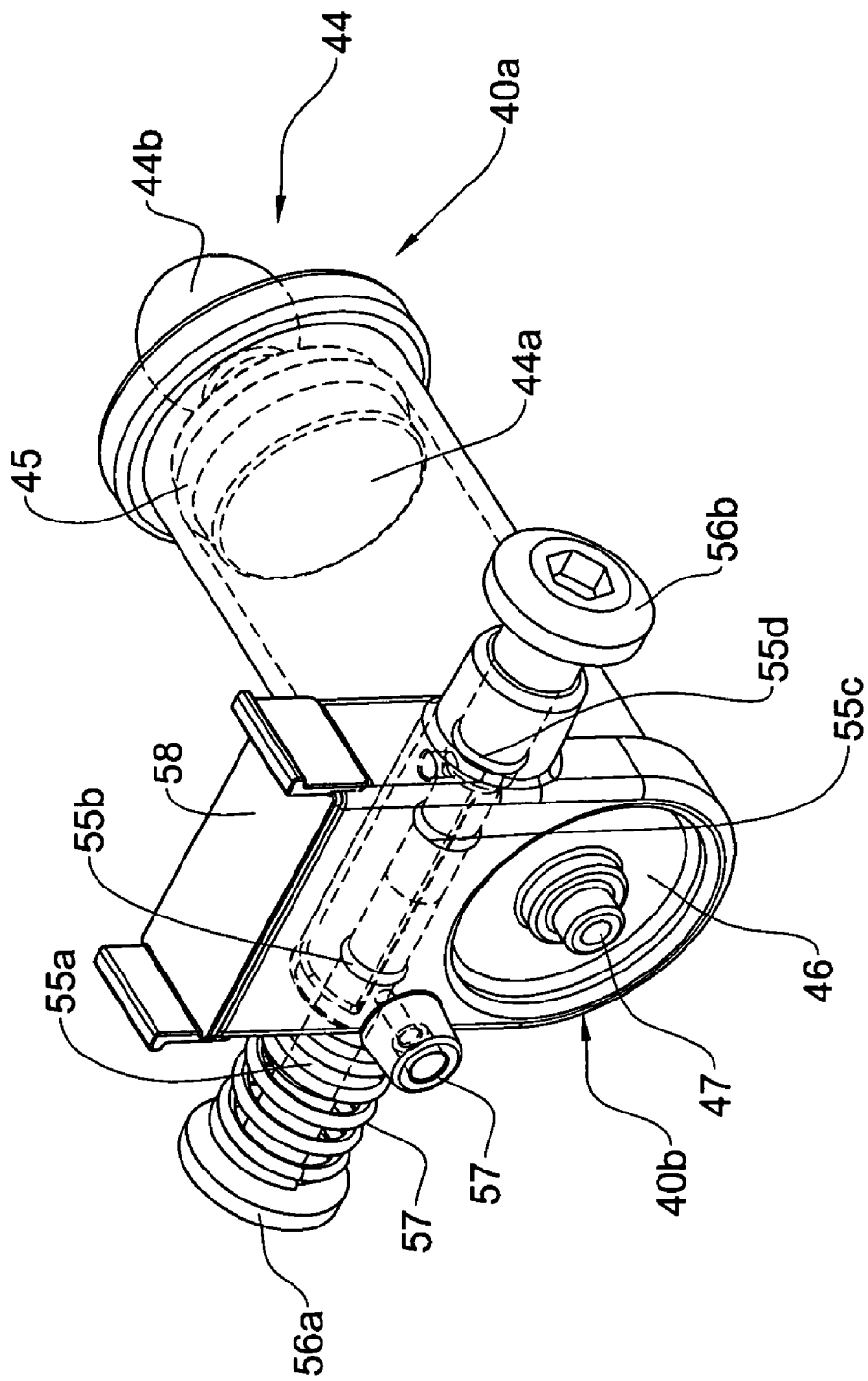
FIG. 2B is a schematic isometric view of the disposable part shown in FIG. 2A in which the body is shown in a transparent form allowing a clear view of the switch-shaft and pressure member used therein.
Figure 2C:
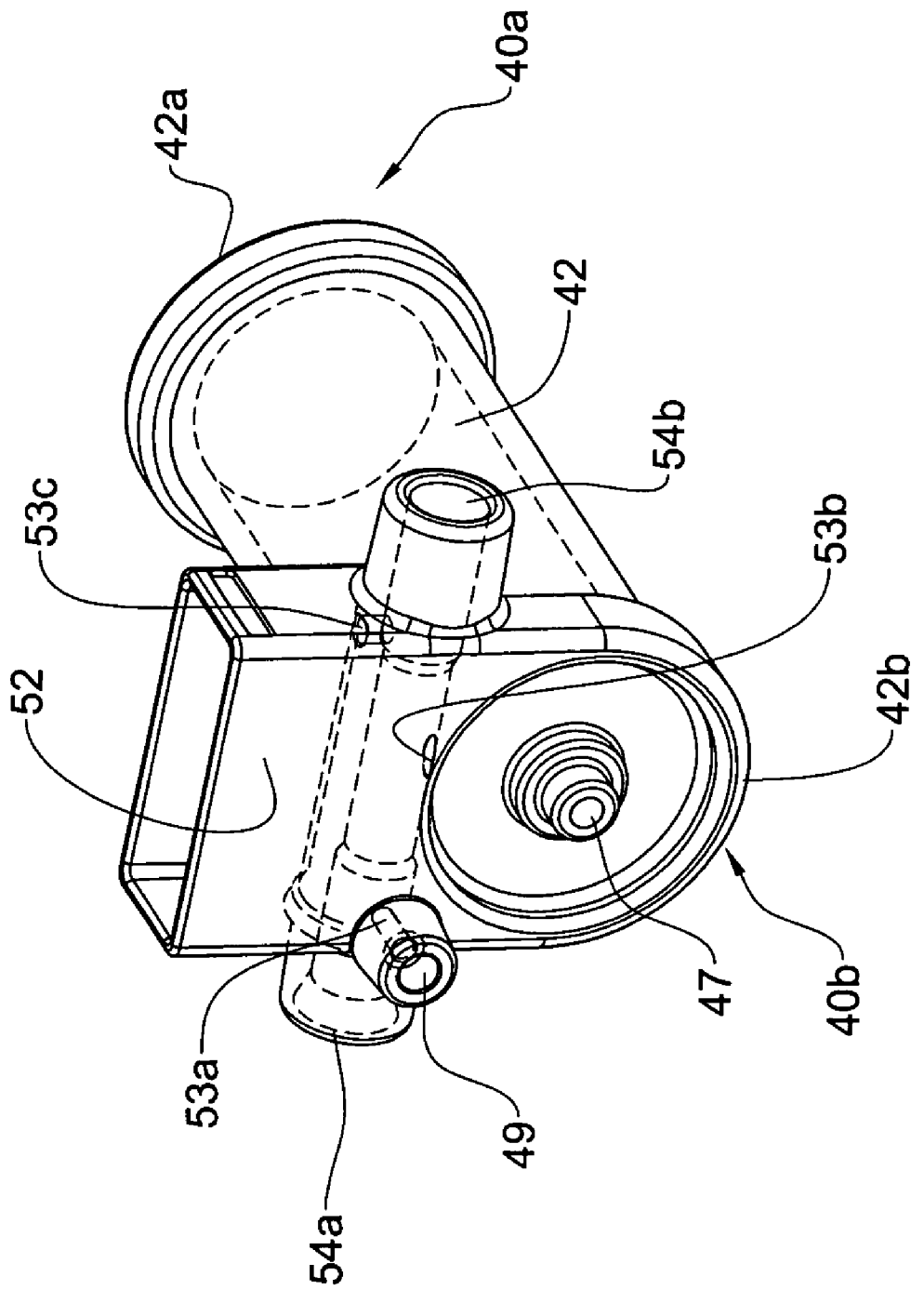
FIG. 2C is a schematic view of the body of the disposable part shown in FIG. 2B.

Turning to FIGS. 2A to 2C, the disposable part 30 comprises a receptacle section 40 with respective distal and proximal portions 40a and 40b, and an optional valve assembly 50 integrally formed with the receptacle adjacent its distal portion 40a. In the detailed description presented below, the receptacle section 40 and the base 20 will be described first and the optional valve assembly 50 will be described thereafter.

The receptacle section 40 is in the form of a hollow barrel 42 with a pressure application end 42a at the proximal portion 40a of the receptacle and a discharge end 42b at the distal portion 40b of the receptacle. The pressure end 42a of the housing is open and is adapted to receive therethrough a pressure member in the form of a piston 44 (FIG. 2B).

The piston 44 is formed of a substantially cylindrical portion 44a and an actuator interface 44b (FIG. 2B). The cylindrical portion 44a is formed with a groove adapted to receive therein an O-ring 45 adapted to prevent leakage of inflation fluid between the inner walls of the barrel 42 and the piston 44. The actuator interface 44b is adapted to be attached to an actuator (not shown in FIGS. 2A to 2C) for multi-use part the displacement of the piston 44 within the barrel 42 as will be explained in detail further on.

The discharge end 42b of the barrel 42 is formed with a resilient diaphragm 46 having an attachment port 47, adapted for attachment thereto of a sensor (shown FIG. 3) for measuring the deformation of the diaphragm 46, which is mounted in the support section 20a of the base 20, as will be described in more detail below.

Figure 3:
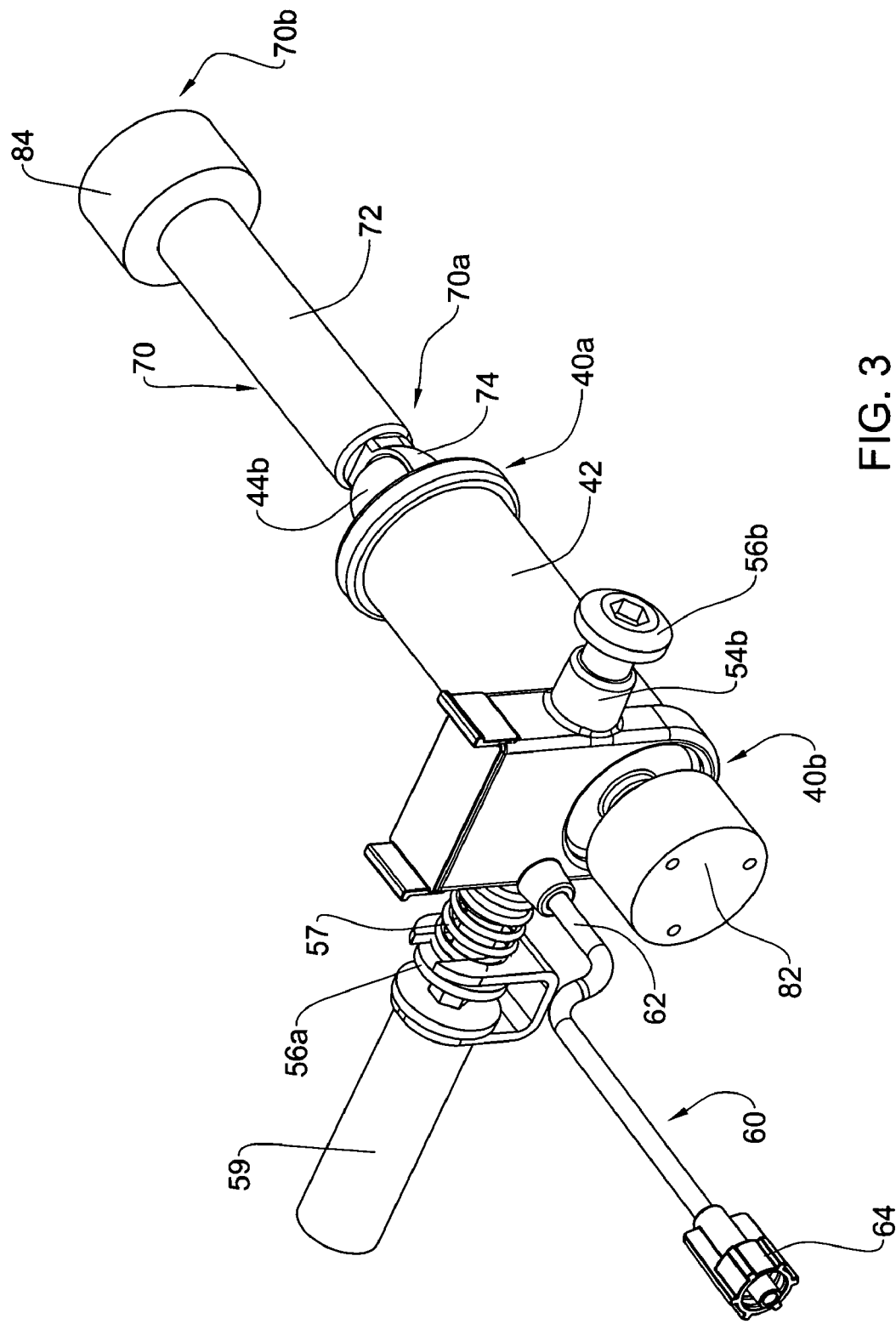
FIG. 3 is a schematic isometric view of the disposable part shown in FIGS. 2A to 2C and attached thereto several elements of the multi-use part of the sensing/activating system of the inflation/deflation system of FIG. 1.

Reverting to FIG. 1, the actuation section 22 has a housing 22 and disposed therein an actuator 70 shown FIG. 3, a motor 21 and a controller (not shown) connectable to a computer and a visual display. The actuator 70 has one end (not seen) at which it is attached to the motor 21 and the other end 70a is formed with a ball socket 74 for detachably receiving therein the actuator interface 44b of the piston 44. The actuator 70 is adapted to be axially displaced within the housing 22 along the central axis X between a fully retracted position and a fully extended position in which the member 72 protrudes from the housing 22 through a hole 23 formed therein into the proximal portion 40a of the receptacle 40, thereby providing support for the proximal end 30a of the disposable part 30.

The support section 24 extends along and is disposed below the level of the axis X, and has its one end portion 24a attached to or integrally formed with the actuation section 20a and the other end portion 24b formed with a vertically projecting support arm 25. The support arm 25 is formed with a tube 26 aligned with the central axis X and adapted to receive therein the distal portion 40b of the receptacle 40 with its diaphragm 46, thereby providing support for the distal end of the disposable part 30.

With reference also to FIG. 3, the base 20 further comprises a sensing system 80 including a first load cell 82 and a second load cell 84, both adapted to measure pressure applied to inflation liquid when filling the hollow barrel 42. The first load cell 82 is associated with the actuator 70 to measure pressure exerted thereby on the piston 44, 70, and the second load cell 84 is positioned within the tube 26 and is adapted to be attached to the attachment port 47 of the resilient diaphragm 46 at the distal end of the receptacle 40 to measure deformation of the resilient diaphragm when pressure is applied to the inflation liquid Both load cells are adapted to transfer data measured thereby to the controller disposed inside the actuating section 20a of the system.

The sensing system 80 further comprises a movement sensor (not shown) associated with the actuator 70 allowing the sensing system 80 to acquire information regarding the axial displacement of the piston 44 within the barrel 42. Based on the data received from the movement sensor, a data processing unit (not shown) positioned within the base 20 is adapted to calculate the volume V of the fluid which is transferred through the discharge end 42b of the barrel 42. It should also be noted that the volume V may be calculated in a variety of ways using data derived from a variety of sensors, for example, by measuring RPM of the motor 21 or by a sterile consumption sensor.

The sensing system 80 as described above allows measuring pressure within the barrel 42 and volume of inflation fluid introduced into the dilatation balloon in a completely non-contact manner, wherein the inflation fluid may remain sterile.

Reverting to FIG. 1, the support section 24 may optionally be made of a first and a second part (not shown) whereby the first part is attached to the barrel 42 and the second part is attached to the piston 44. The base 20 further comprises an emergency release mechanism 28 for quick release of the dilatation balloon from the blood vessel in case of a malfunction such as rupture of the balloon, rupture of the blood vessel or even in the event of a power cut. The release mechanism 28 operates in a completely mechanical manner and does not rely on a power supply to perform the release. In case of an emergency release of the disposable part 30 from the base 20, the release mechanism 28 is manually pulled back, displacing the piston 44 and consequently draining the inflation fluid from the dilatation balloon. This may be achieved by separating the first part of the support section from the second part, thereby separating the piston 44 from the barrel 42.

With reference to FIGS. 2B, 2C and 3, the optional valve assembly 50 of the disposable part 30 will now be described which is formed integrally with the receptacle 40 thereof The valve assembly 50 comprises a storage chamber 52 with a lid 58, a channel 54 having a first end 54a and a second end 54b, and three outlets being disposed therealong 53a, 53b and 53c leading to the inlet/outlet port 49, barrel 42 and storage chamber 52 respectively. A switch-shaft 56 is inserted in the channel 54 and comprising a first distribution member 56a at one end thereof associated with the first end 54a of the channel 54 and a second distribution member 56b at the other end thereof associated with the second end 54b of the channel 54.

The distribution members 56a, 56b are adapted to be attached to each other after insertion into the fluid channel 54 by a screwing engagement, and may be axially displaced along the channel 54 so as to switch from one position to another. The switch-shaft 56 is stepped, i.e. tubular steel shaft which tapers in a series of steps, and is fitted with four O-rings 55a to 55d respectively, adapted to prevent leakage of liquid outside the disposable part.

The valve assembly 50 further comprises a biasing spring 57 mounted on the switch-shaft 56 between the first distribution member 56a and the side wall of the storage chamber 52 so as to bias the switch-shaft 56. The switch-shaft 56 is displaceable along the channel 54 by a motor (not shown) to be connected to the first distribution member 56a.

With particular reference being made to FIG. 2C, the barrel 42 and valve 50 are integrally formed so that the outlet 53a is in fluid communication with the inlet/inlet/outlet port 49, the outlet 53b is in fluid communication with the barrel 42, and the outlet 53c is fluid communication with the storage chamber 52.

Thus, the valve assembly 50 is adapted to take several positions depending on the position of the switch-shaft 56 relative to the inlets of the channel 54 as specified below:
  a) first, 'inflation/withdrawal' position, in which fluid communication is provided between the barrel 42 and the inlet/outlet port 49, while fluid communication with the storage chamber 52 is blocked; in this position it is possible to withdraw fluid from an outside source into the barrel 42 or discharge fluid from the barrel 42 outwardly through the inlet/outlet port 49;
  b) second, 'air removal' position, in which fluid communication is provided between the barrel 42 and the storage chamber 52, while fluid communication with the inlet/outlet port 49 is blocked; in this position air bubbles within the inflation fluid may be removed from the fluid by being discharged through the storage chamber 52;
  c) third, 'tuning' position, in which fluid communication is blocked both between the barrel 42 and inlet/outlet port 49 and between the barrel 42 and storage chamber 52; in this position it is possible to tune the sensors 82, 84 by applying pressure to the piston 44 against the resilient diaphragm 46;
  d) fourth, 'discharge' position in which fluid communication is provided between the inlet/outlet port 49 and barrel 42 to the outside environment through said channel 54 by partially removing said switch shaft 56 therefrom; in this position it is possible to manually release the balloon in case of an emergency;

Position 'd' is achieved when the switch-shaft 56 is pushed inwards, i.e. the spring 57 compresses, to such an extent that the O-rings 55c and 55d are displaced outside the channel 54, thus no longer sealing the valve assembly 50 and allowing leakage of fluid from the channel 54 to the outside environment. In practice, such a position of the switch-shaft 56 allows the fluid to be discharged from the barrel 42, storage chamber 52 and dilatation balloon through the second end of the channel 54b.

In assembly of the inflation/deflation system 10 described above, before performing a dilatation procedure, the disposable part 30 is mounted on the base 20 such that the ball 44b of the piston 44 is received in the socket 74 of actuator 70, the distribution member 56a of the switch-shaft 56 is connected to another motor of the actuation section 20a and the distal end 40b of the receptacle section 40 is received within the tube 26 of the support section 20b so that the attachment port 47 becomes attached to the sensor 82.

In preparation to the dilatation procedure, the supply line 60 is attached at its first end 62 to the inlet/inlet/outlet port 49 of the disposable part 40, and at its second end 64 to a supply of a contrast fluid. The position of the valve assembly 50 is then switched to an 'inflation/withdrawal' position and the piston 44 is displaced by the actuator 70, allowing the contrast fluid to flow into the barrel 42. Once the contrast fluid has been introduced into the barrel 42, the position of the valve assembly 50 is switched to an 'air removal' position. In this position the piston 44 is pushed forward pressuring the contrast fluid into the storage chamber 52 of the valve assembly 50 allowing excess air bubbles to be discharged from the contrast fluid to the outside environment.

Next, the second end 64 of the supply line 60 is attached to a supply of a diluting liquid and the position of the valve assembly 50 is again switched to the 'inflation/withdrawal' position and the diluting fluid is introduced into the barrel 42. The valve assembly 50 is then switched back into an 'air removal' position and the piston 44 is again pushed into the barrel 42 pressuring both fluids into the storage chamber 52. This allows the removal of air bubbles from the fluids as well as mixture of the contrast and diluting fluid to form a uniform mix. Thereafter the uniform mix is returned into the barrel 42 by displacing the piston 44 such that the mix is entirely within the barrel 42. During withdrawal of the mix into the barrel 42 air is simultaneously withdrawn from the balloon, causing it to shrink and allowing it to assume a dimension small enough to be inserted into the desired blood vessel.

Concluding the preparation stage is the tuning of the system 10. In order to tune the system 10 the valve assembly 50 is switched into a 'tuning' position in which fluid communication of the inlet/outlet port 49 and storage chamber 52 with the barrel 42 is blocked. The piston 44 is then displaced back and forth repeatedly, allowing the sensing system to receive data from the sensors and tune the system 10.

Once the preparation stage is complete, a dilatation balloon (not shown) may be attached to the inlet/outlet tube 60 mounted on the inlet/outlet port 49 of the receptacle section 40. The valve assembly 50 may then be switched into an 'inflation/withdrawal' position and the piston 44 is pulled backwards facilitating removal of air from the dilatation balloon by withdrawing it into the barrel 42. The withdrawn air may be discharged through the storage chamber 52 in the 'air removal' position.

Finally, the system 10 is ready for the inflation stage, wherein the inflation fluid is introduced into the dilatation balloon. The motor operates the actuator 70 such that the piston 44 is displaced along the barrel 42, thus pressing the inflation fluid into the balloon. Since the actuator 70 is both attached to the piston 44 and associated with the sensing system 80, real-time data regarding the time of inflation and the volume of the inflation fluid introduced into the balloon, and pressure within the barrel may be derived.

The controller of the system may be programmed to automatically react to changes in pressure according to data derived from the sensing system 80. For example, a predetermined maximum pressure value may be set wherein, in case the controller receives information from the sensing system that the pressure reaches the maximum pressure, it may slow down the motor or stop it completely in order not to exceed the predetermined value.

Figure 4A:
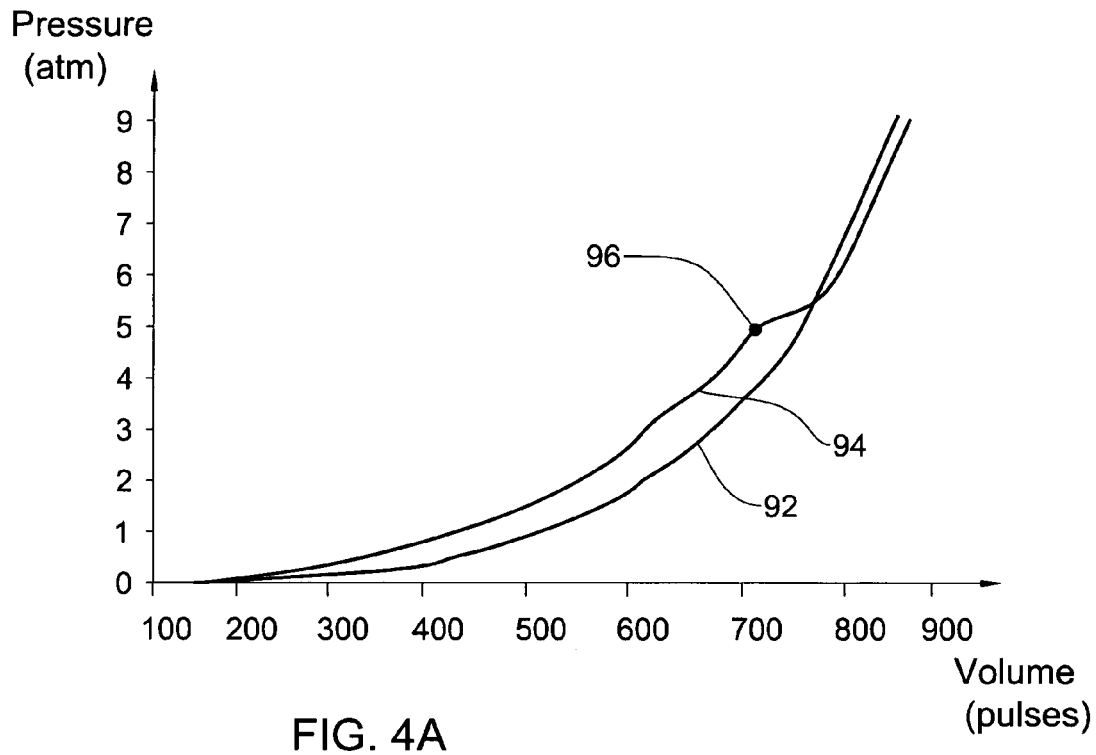
FIGS. 4A and 4B are schematic views of P vs. V and P vs. T schemes made according to data derived from the sensing system shown in FIG. 3.
Figure 4B:
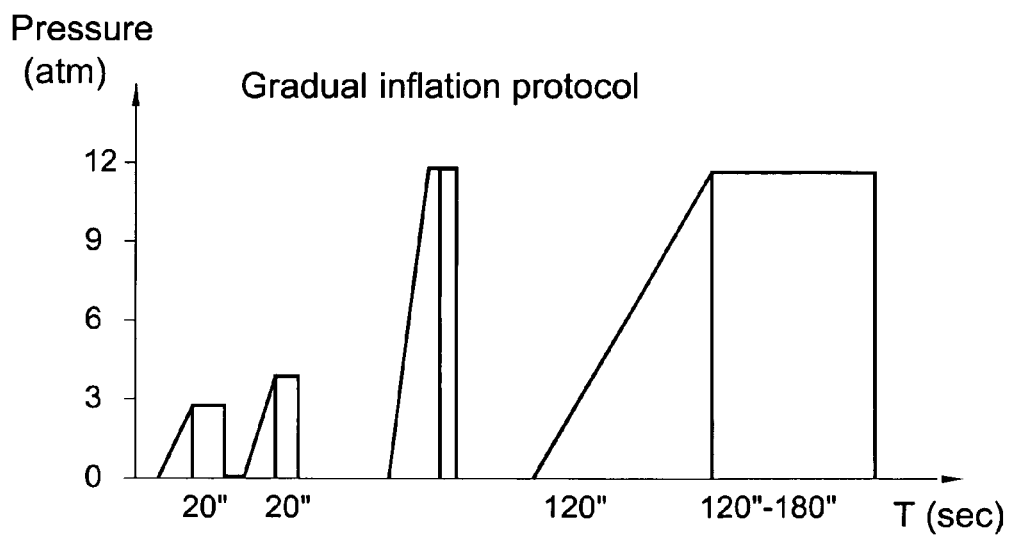

Turning to FIGS. 4A and 4B, several schemes of pressure P vs. volume V and pressure P vs. time T are shown, respectively. The first P vs. V scheme 92 is a scheme produced during a standard catheterization process. It may be observed that the pressure within the balloon increases as a function of inflation fluid leaving the barrel 42. In this essence it should be noted that the sensing system receives a reading indicating the amount of fluid promoted by the piston 44 and calculating the amount of fluid within the dilatation balloon.

The second P vs. V scheme 94 is produced during a similar catheterization system in which the blood vessel has its inner walls covered by a layer of plaque (not shown). As more inflation fluid is introduced into the balloon, the balloon exerts more and more pressure on the inner walls of blood vessel by direct contact with the plaque layer.

However, as pressure on the plaque layer increases, it begins to crack and eventually reaches a breaking point 96. In its broken form, the pieces of the plaque are pressed against the inner wall of the blood vessel causing increased sensitivity thereof and may thus damage it. Once the breaking point 96 is achieved, the balloon may further dilate allowing more inflation fluid to pour therein, facilitating a pressure drop. This phenomenon may be clearly noticeable from the temporary slope drop in the P vs. V line 94 after point 96. Thus, when such a phenomenon is noticed the inflation rate may be automatically changed so as not to damage the blood vessel.

Those skilled in the art to which this invention pertains will readily appreciate that numerous changes, variations, and modifications can be made without departing from the scope of the invention, mutatis mutandis.

The invention claimed is:

1. An inflation/deflation system for a dilatation balloon, said system comprising:
    a) a receptacle adapted to contain an inflation fluid to be introduced into said balloon during its inflation, said receptacle having an inlet/outlet port adapted for connection to said dilatation balloon;
    b) a pressure member adapted to be axially displaced within said receptacle to cause said fluid to exit the receptacle via said outlet port;
    c) a sensing system comprising a first sensor associated with said pressure member to sense its axial displacement, a second sensor associated with the interior of said receptacle to sense in a non-contact manner the pressure P of the inflation fluid within said receptacle, and an additional sensor associated with the pressure member to sense the pressure on the pressure member during said axial displacement for comparing it with the pressure of the inflation fluid within the receptacle; and
    d) a data processing and display unit adapted to process signals from the sensors and display at least a scheme of pressure P within said receptacle vs. the volume V of the inflation fluid exiting said receptacle through said inlet/outlet port, calculated by said axial displacement, said scheme reflecting the corresponding P-V conditions within the balloon when the system is in use.

2. A system according to claim 1, wherein the first sensor of the sensing system is associated with the pressure member and adapted to measure its axial displacement, and provides data allowing calculation of the volume V of fluid exiting the receptacle and consequently introduced into the balloon.

3. A system according to claim 1, wherein the second sensor of the sensing system is attached to said receptacle and adapted to calculate the pressure of the fluid therein in a non-contact manner.

4. A system according to claim 3, wherein said receptacle has a pressure sensitive surface and said second sensor is in the form of a load cell attached to said surface to sense the load exerted thereon by the fluid within the receptacle.

5. A system according to claim 4, wherein said pressure sensitive surface is in the form of a resilient diaphragm.

6. A system according to claim 1, wherein said P-V scheme indicates breakage of plaque along the blood vessel being dilated, possible rupture of the dilatation balloon, a minor puncture therein, and/or leakage in any other part of the system.

7. A system according to claim 1, wherein said system further comprises a control unit associated on one hand with the data processing and display unit and adapted to receive processed data therefrom, and on the other hand with the pressure member in order to control it.

8. A system according to claim 7, wherein the operation of said system is pre-programmed according to a desired P-T curve.

9. A system according to claim 7, wherein said system is configured for working in predetermined cycles according to preset time and pressure parameters.

10. A system according to claim 1, wherein said system comprises a base and a disposable part.

11. A system according to claim 10, wherein said base contains an actuation section comprising an actuator for moving said pressure member and being disposed within a housing.

12. A system according to claim 10, wherein said base further comprises at least said sensing system.

13. A system according to claim 11, wherein said base further comprises a motor associated with said actuator and disposed within said housing.

14. A system according to claim 13, wherein said motor is associated with said first sensor in order to indirectly provide data about axial displacement of the pressure member, and subsequently allows calculation of volume of inflation fluid discharged during the dilatation process.

15. A system according to claim 10, wherein said base further comprises a quick release mechanism allowing manual release of the pressure member from the receptacle without the use of a motor.

16. A system according to claim 15, wherein the housing of said base is made of a first part adapted for connection thereto of said receptacle and a second part adapted for connection thereto of said pressure member, and wherein said release is achieved by separation of said first part from said second part.

17. A system according to claim 10, wherein said disposable part comprises the receptacle and the pressure member.

18. A system according to claim 17, wherein said receptacle is in the form of a syringe barrel and said pressure member is in the form of a syringe piston positioned therein.

19. A system according to claim 10, wherein said disposable part further comprises a disposable four-way valve, comprising a main channel having at least a first, a second and a third port, a switch shaft adapted to axially displace therein to alternately open/close said ports.

20. A system according to claim 19, wherein said valve further comprises a storage chamber being in fluid communication with said channel through one of said ports, and adapted for removal of air from the inflation liquid.

21. A system according to claim 20, wherein said storage chamber further comprises at least one additional port adapted to allow discharge of air from the inflation fluid to the outside environment.

22. A system according to claim 19, wherein one of said first, second and third ports is in fluid communication with the barrel of said receptacle.

23. A system according to claim 19, wherein said valve is integrally formed with the receptacle to form said disposable part.

24. A system according to claim 23, wherein one of said ports constitutes the inlet/outlet port of said receptacle.

25. A system according to claim 20, wherein said valve may assume one of the following four positions:
   a) 'inflation/withdrawal'—fluid communication is provided between the receptacle and the inlet/outlet port, while fluid communication with the storage chamber is blocked, allowing to withdraw inflation fluid from an outside source or administering it into the balloon;
   b) 'air removal'—fluid communication is provided between the receptacle and the storage chamber, while fluid communication with the inlet/outlet port is blocked, allowing removal of air from the inflation fluid through the storage chamber;
   c) 'tuning'—fluid communication is blocked both between the receptacle and inlet/outlet port and between the receptacle and storage chamber, allowing tuning of the load cells; and
   d) 'discharge'—fluid communication is provided between the inlet/outlet port, and receptacle to the outside environment through said channel, allowing removal of inflation fluid from the system during an emergency.

26. A system according to claim 19, wherein said switch-shaft is adapted to be displaced within the channel by a driving member disposed in the housing of the actuation section of the base.

27. A system according to claim 26, wherein said driving member is an auxiliary motor.

28. A system according to claim 10, wherein said disposable part is in the form of a 'ready to use' kit wherein the receptacle already contains the inflation fluid.

29. A disposable kit for use with a base of an inflation/deflation system adapted for inflation of a dilatation balloon, and comprising: a receptacle adapted to contain an inflation fluid to be introduced into said balloon during its inflation, said receptacle having an inlet/outlet port adapted for connection to said dilatation balloon; a pressure member adapted to be axially displaced within said receptacle to cause said fluid to exit the receptacle via said outlet port; the base of said system comprising: a sensing system comprising a first sensor associated with said pressure member to sense its axial displacement, a second sensor associated with the interior of said receptacle to sense in a non-contact manner the pressure P of the inflation fluid within said receptacle, and an additional sensor associated with the pressure member to sense the pressure on the pressure member during said axial displacement for comparing it with the pressure of the inflation fluid within the receptacle; and a data processing and display unit adapted to process signals from the sensors and display at least a scheme of pressure P within said receptacle vs. the volume V of the inflation fluid exiting said receptacle through said inlet/outlet port, calculated by said axial displacement, said scheme reflecting the corresponding P-V conditions within the balloon when the system is in use.

30. A multi-use base for use in an inflation/deflation system for inflation of a dilatation balloon, with a disposable part comprising: a receptacle adapted to contain an inflation fluid to be introduced into said balloon during its inflation, said receptacle having an inlet/outlet port adapted for connection to said dilatation balloon; a pressure member adapted to be axially displaced within said receptacle to cause said fluid to exit the receptacle via said outlet port; said multi-use part comprising: a sensing system comprising a first sensor associated with said pressure member to sense its axial displacement, a second sensor associated with the interior of said receptacle to sense in a non-contact manner the pressure P of the inflation fluid within said receptacle, and an additional sensor associated with the pressure member to sense the pressure on the pressure member during said axial displacement for comparing it with the pressure of the inflation fluid within the receptacle; and a data processing and display unit adapted to process signals from the sensors and display at least a scheme of pressure P within said receptacle vs. the volume V of the inflation fluid exiting said receptacle through said inlet/outlet port, calculated by said axial displacement, said scheme reflecting the corresponding P-V conditions within the balloon when the system is in use.

* * * * *